United States Patent [19]

Ragland et al.

[11] Patent Number: 6,127,115
[45] Date of Patent: Oct. 3, 2000

[54] EFFICIENT METHOD OF DETECTING AN INFECTIOUS AGENT IN BLOOD

[76] Inventors: William L. Ragland, 107 Sena Dr., Athens, Ga. 30605; Mark A. Goodwin, 160 Lawrenceville Ave., Jefferson, Ga. 30549; Renata Novak, 180 Cross Creek Pl., Aptartment #4, Athens, Ga. 30605

[21] Appl. No.: 08/749,157

[22] Filed: Nov. 14, 1996

Related U.S. Application Data

[60] Provisional application No. 60/006,698, Nov. 14, 1995.
[51] Int. Cl.$^7$ .............................. C12Q 1/70; C12Q 1/68; C07H 21/04
[52] U.S. Cl. ................... 435/6; 435/5; 435/6; 536/24.32; 536/25.32
[58] Field of Search ........................ 435/5, 6; 536/25.32, 536/24.32

[56] References Cited

U.S. PATENT DOCUMENTS

| | | | |
|---|---|---|---|
| 5,008,182 | 4/1991 | Sninsky et al. | 435/5 |
| 5,225,326 | 7/1993 | Bresser et al. | 435/6 |
| 5,491,073 | 2/1996 | Noteborn et al. | 435/6 |
| 5,538,871 | 7/1996 | Nuovo et al. | 435/91.2 |

FOREIGN PATENT DOCUMENTS

| | | |
|---|---|---|
| 0 192 168 | 8/1986 | European Pat. Off. . |
| 0 219 842 A2 | 4/1987 | European Pat. Off. . |
| 0 483 911 A2 | 5/1992 | WIPO . |
| 9603507A1 | 2/1996 | WIPO . |

OTHER PUBLICATIONS

Anon Detection of transgenic animals without cell culture using fluorescence in situ hybridization Bio Techniquew, vol. 18 (6), p. 952, 954 and 956, 1995.
Ven Den Berg et al. Detection of different developmental stages of malaria parasites by non–radioactive DNA in situ hybridization Histochemical Journal vol. 23, p. 109–115, 1991.
Gunseberg et al. Competitive Assay to Improve the Specificity of Detection of Single–Point Mutation in $\alpha_1$–Antitypsin Deficiency, Clinical Chemistry 39(10) p. 2157–2162, (1993).
Allen et al. In situ hybridization for the detection of chicken anemia virus in formalin–fixed paraffin–embedded sections Avian Diseases vol. 37, p. 177–183, 1993.
Zawatzky et al. Identification of individual interferon–producing cells by in situ hybridization, Proc. Natl. Acad. Sci. USA, vol. 82 p. 1136–1140, 1985.
Daniele Chevrier, et al., PCR Product Quantification by Non–radioactive Hybridization Procedures using an Oligonucleotide Covalently Bound to Microwells, 1993 Academic Press Limited, *Molecular and Cellular Probes* (1993) 7, 187–197.
Jean–Robert Deverre, et al., A Competitive Enzyme Hybridization Assay for Plasma Determination of Phosphodiester and Phosphorothioate Antisense Oligonucleotides, 1997 Oxford University Press, 3584–3589 *Nucleic Acids Research*, 1997, vol. 25, No. 18.

Yuasa et al., "Isolation and some characteristics of an agent inducing anemia in chicks," *Avian Diseases*, vol. 23, pp. 366–385 (1979).
Gelderblom et al., "Morphological characterization of chicken anemia agent (CAA)," *Archives of Virology*, vol. 109, pp. 115–120 (1989).
Todd et al., "Purification and biochemical characterization of chicken anemia agent," *Journal of General Virology*, vol. 71, pp. 819–823 (1990).
Taniguchi et al., "Haematopathological changes in dead and moribund chicks induced by chicken anemia agent," *National Institute of Animal Health Quarterly*, Japan, vol. 22, pp. 61–69 (1982).
Taniguchi et al., "Chronological observations on hemato–pathological changes in chicks inoculated with chicken anemia agent," *National Institute of Animal Health Quarterly*, Japan, vol. 23, pp. 1–12 (1983).
Bulow et al., "Untersuchungen uber den Erreger der infektiosen Anamie bie Huhnerkuken (CAA) in vitro: Vermehrung, Titration, Serumneutralisationstest und indirekter Immunofluoreszenztest," *Zbl. of Veterinary Medicine, B*, vol. 32, pp. 679–693 (1985).
Yuasa et al., "Aetiological examination of an outbreak of haemorrhagic syndrome in a broiler flock in Japan," *Avian Pathology*, vol. 16, pp. 521–526 (1987).
Jeurissen et al., "Transient depletion of cortical thymocytes induced by chicken anemia agent," *Thymus*, vol. 14, pp. 115–123 (1989).
Otaki et al., "Isolation of chicken anemia agent and Marek's disease virus from chickens vaccinated with turkey herpesvirus and lesions induced in chicks by inoculating both agents," *Avian Pathology*, vol. 16, pp. 291–306 (1987).
Cloud et al., "Immune dysfunction following infection with chicken anemia agent and infectious bursal disease virus I. Kinetic alterations of avian lymphocyte subpopulations," *Veterinary Immunology and Immunopathology*, vol. 34, pp. 3337–3352 (1992).
Cloud et al, "Immune dysfunction following infection with chicken anemia agent and infectious bursal disease virus II. Alterations of in vitro lymphoproliferation and in vivo immune responses," *Veterinary Immunology and Immunopathology*, vol. 34, pp. 353–366 (1992).

(List continued on next page.)

*Primary Examiner*—W. Gary Jones
*Assistant Examiner*—Joyce Tung
*Attorney, Agent, or Firm*—Jones & Askew, LLP

[57] ABSTRACT

The present invention provides a method for detecting the presence of a predetermined infectious agent in a human or animal subject comprising obtaining a preselected portion of a whole blood sample containing at least one intact blood cell from the subject and detecting the presence of a nucleic acid from the predetermined infectious agent in the intact blood cell by nucleic acid hybridization. The preselected portion of the blood sample can include any portion which contains at least one intact blood cell, for example a peripheral blood smear or cytospin buffy coat preparation. The intact blood cell can be any blood cell including, but not limited to white blood cells and red blood cells. In one embodiment, the blood cell is a lymphocyte.

6 Claims, No Drawings

OTHER PUBLICATIONS

Bounous et al., "Immunosuppression and intracellular calcium signaling in splenocytes from chicks infected with chicken anemia virus, CL–1 isolate," *Avian Diseases*, vol. 39, pp. 135–140 (1995).

Yuasa et al., "Effect of infectious bursal disease virus infection on incidence of anemia by chicken anemia agent," *Avian Diseases*, vol. 24, pp. 202–209 (1980).

Bulow et al., "Folgen der Doppelinfektion von Kuken mit Adenovirus oder Reovirus und dem Erreger der aviaren infektiosen Anamie (CAA)," *Journal of Veterinary Medicine, B*, vol. 33, pp. 717–726 (1986).

Engstrom, B.E., "Blue wing disease of chickens: Isolation of avaian reovirus and chicken anaemia agent," *Avian Pathology*, vol. 17, pp. 23–32 (1988).

Rosenberger et al., "The effects of age, route of exposure, and coinfection with infectious bursal disease virus on the pathogenicity and transmissibility of chicken anemia agent (CAA)," *Avian Diseases*, vol. 33, pp. 753–759 (1989).

Rosenberger et al., "The isolation and characterization of chicken anemia agent (CAA) from broilers in the United States," *Avian Diseases*, vol. 33, pp. 707–713 (1989).

McNulty et al., "Applications of immunofluorescence in veterinary viral diagnosis," *Recent advances in virus diagnosis*. (McNulty & McFerran, eds.), The Hague: Martinus Nijhoff, Netherlands, pp. 15–26 (1984).

Noteborn et al., "Detection of chicken anaemia virus by DNA hybridization and polymerase chain reaction," *Avian Pathology*, vol. 21, pp. 107–118 (1992).

Allan et al., "In situ hybridization for the detection of chicken anemia in formalin–fixed, paraffin–embedded sections," *Avian Diseases*, vol. 37, pp. 177–182 (1993).

Noteborn et al., "Characterization of cloned chicken anemia virus DNA that contains all elements for the infectious replication cycle," *Journal of Virology*, vol. 65, pp. 3131–3139 (1991).

Sambrook et al., "Molecular cloning: a laboratory manual (Second Edition)," Cold Spring Harbor Laboratory, Cold Spring Harbor, N.Y., 1989.

McGadey, J., "A tetrazolium method for non–specific alkaline phosphatase," *Histochimie*, vol. 23, pp. 180–184 (1970).

Yuasa et al., "Isolation of chicken anemia agent with MDC-C–MSB1 cells from chickens in the field," *National Institute of Animal Health Quarterly, Japan*, vol. 23, pp. 75–77 (1983).

Mitchell et al., "In situ hybridization: a review of methodologies and applications in the biomedical sciences," *Medical Laboratory Sciences*, vol. 49, pp. 107–118 (1992).

Martinez et al., "Non–radioactive Localization of Nucleic Acids by Direct In Situ PCR and In Situ RT–PCR in Paraffin–embedded Sections," *Journal of Histochemistry and Cytochemistry*, vol. 43, No. 0, pp. 0–00, 1995.

Todd et al., "Development of an enzyme–linked immunosorbent assay to detect serum antibody to chicken anemia agent," *Avian Diseases*, vol. 34, pp. 359–363 (1990).

Noteborn et al., "Chicken anemia virus infection: molecular basis of pathogenicity," *Avian Pathology*, vol. 24, pp. 11–31 (1995).

McNulty et al., "Economic effects of subclinical chicken anemia agent infection in broiler chickens," *Avian Diseases*, vol. 35, pp. 263–268 (1991).

Yuasa et al., "Survey of antibody against chicken anaemia agent (CAA) by an indirect immunofluorescent antibody technique in breeder flocks in Japan," *Avian Pathology*, vol. 14, pp. 521–530 (1985).

Chan, V. T–W, Extraction of nucleic acids from clinical samples and cultured cells. In *Diagnostic molecular pathology: a practical approach*. (Herrington et al., eds.), vol. 2, pp. 1–23, New York: Oxford University Press, 1992.

Herrington et al., Principles and basic methodology of DNA/RNA detection by in situ hybridization. In *Diagnostic molecular pathology: a practical approach* (Herrington et al. eds.), vol. 1, pp. 69–102, New York: Oxford University Press, 1992.

Winberg, G., "A rapid method for preparing DNA from blood, suited for PCR screening on transgenes in mice," *PCR—Methods and Applications*, vol. 1, pp. 72–74 (1991).

Cuypers et al., "Storage conditions of blood samples and primer selection affect the yield of cDNA polymerase chain reaction products of hepatitis C virus," *Journal of Clinical Microbiology*, vol. 30, pp. 3220–3224 (1992).

Pope, C.R., "Chicken anemia agent," *Veterinary Immunology and Immunopathology*, vol. 30, pp. 51–65 (1991).

Yuasa et al., "Distribution of chicken anemia agent (CAA) and detection of neutralizing antibody in chicks experimentally inoculated with CAA," *National Institute of Animal Health Quarterly, Japan*, vol. 23, pp. 78–81 (1983).

Ge et al., "Detection of *Anaplasma marginale* DNA in bovine erythrocytes by slot–blot and in situ hybridization with a PCR–mediated digoxigenin–labeled DNA probe," *Journal of Veterinary Diagnostic Investigation*, vol. 7, pp. 465–472 (1995).

Kumar et al., "A Method for the Rapid Screening of Human Blood Samples for the Presence of HIV–1 Sequences: The Probe Shift Assay," *AIDS Research and Human Retroviruses*, vol. 5, No. 3, pp. 345–354 Mary Ann Liebert, Inc., Publishers (1989).

Brigati et al., "Detection of Viral Genomes in Cultured Cells and Paraffin–Embedded Tissue Sections Using Biotin–Labeled Hybridization Probes," *Virology*, vol. 126, pp. 32–50 (1983).

Niagro et al., "Infection of circulating mononuclear cells by psittacine beak and feather disease virus," (Abstract), from *Interscience Conference on Antimicrobial Agents and Chemotherapy*, vol. 30 p. 291,(1990).

Rubin et al., "Newborn Screening by DNA analysis of dried blood spots," *Human Genetics*, vol. 82, pp. 134–136, (1989).

EFFICIENT METHOD OF DETECTING AN INFECTIOUS AGENT IN BLOOD

CROSS-REFERENCE TO RELATED PATENT APPLICATIONS

This application claims the benefit of U.S. Provisional Application Ser. No. 60/006,698 filed on Nov. 14, 1995.

FIELD OF THE INVENTION

The present invention relates to the field of rapid detection and diagnosis of an infectious agents in a subject utilizing a nucleic acid amplification technique performed directly on intact blood cells in a blood sample obtained from the subject.

BACKGROUND OF THE INVENTION

Detection of nucleic acids has an important role in diagnosis of a variety of diseases. The conventional molecular techniques for detection of nucleic acids are usually time consuming and require laborious preparation of samples, including nucleic acid extraction. The use of those harsh procedures results in destruction of cellular morphology, which is a great disadvantage in cases when cellular localization of specific sequences is of particular interest.

Chicken anemia virus (CAV), formerly called chicken anemia agent (CAA), was first isolated by Yuasa et al.[1] and its viral particles were found to contain circular single-stranded DNA[2,3]. CAV causes severe aplastic anemia in chickens[1,4,5], depletion of lymphoid organs, subcutaneous and intramuscular hemorrhages, and destruction of erythroblastoid cells in bone marrow[6,7,8]. Immune suppression caused by CAV infection is among the most important aspects of the disease[9,10,11,12]. In the field, CAV causes more serious problems when associated with other viruses[13,14,15,16,17].

Current diagnostic tests for CAV are based on serological methods using neutralization tests[6], ELISA[3] and immunofluorescence assays[18]. Noteborn et al.[19] reported two additional tests: polymerase chain reaction (PCR) and a dot-blot assay, using digoxigenin-labeled c-CAV DNA as probe on CAV isolates propagated in the lymphoblastoid T-cell line, MDCC-MSB1. Allan et al.[20] compared the immunocytochemical method for detection of CAV antibodies and in situ hybridization technique for localization of CAV on formalin-fixed and paraffin-embedded thymus tissue.

Prior to the present invention, isolation of CAV in cell cultures[24] and the aforementioned immunofluorescence assays[18], ELISA's[3], and detection of virus by PCR and by in situ hybridization in formalin-fixed and paraffin-embedded thymus tissue[20], have been methods of choice in laboratory diagnosis of chicken anemia. However, isolation of the virus is an extremely time-consuming procedure and not always the most appropriate because diagnosis is usually required in short period of time. Immunofluorescence assays can be carried out only if specialized equipment is available as well experienced personnel, which is often not the case in diagnostic laboratories. Serological tests should be supplemented by antigen or nucleic acid detection in cases of inadequate immune response to acute infection by immunocompromised individuals.

When immunocytochemical methods are used for detection of virus in tissue, the main obstacle is cross-linking of proteins and subsequent masking of viral antigen as a result of routine formalin fixation of tissue following post mortem examination. The loss of antigenicity can be somewhat reversed by treatment with proteolytic enzymes but this is of limited use for CAV[20]. In situ hybridization method for detection of CAV in tissue sections, although not impaired following long fixation time, requires conventional tissue preparation including paraffin embedment and tissue sectioning that delays diagnosis.

The present study describes in situ hybridization technique for detection of CAV DNA in blood smears. This method utilizes very simple and cost effective sample collection and preparation, and is applicable for wide use in the field for rapid diagnosis of any infectious agent that is present in whole blood cells.

SUMMARY OF THE INVENTION

The present invention provides a method for detecting the presence of a predetermined infectious agent in a human or animal subject comprising obtaining a preselected portion of a whole blood sample containing at least one intact blood cell from the subject and detecting the presence of a nucleic acid from the predetermined infectious agent in the intact blood cell by nucleic acid hybridization. The preselected portion of the blood sample can include any portion which contains at least one intact blood cell, for example a peripheral blood smear or cytospin buffy coat preparation. The intact blood cell can be any blood cell including, but not limited to white blood cells and red blood cells. In one embodiment, the blood cell is a lymphocyte.

The predetermined infectious agent can be any virus, bacteria or other agent which infects a blood cell, for example human immunodeficiency viruses (HIV), parvoviruses et al. In particular, the present invention provides a method for detecting the presence of an infectious agent in a subject comprising detecting the presence of a nucleic acid from the infectious agent by utilization of in situ hybridization.

In one embodiment, the invention provides a method of detection for the presence of chicken anemia virus in a chicken comprising utilizing a preselected portion of a whole blood sample containing an intact blood cell, such as a lymphocyte obtained from the chicken and detecting the presence of a nucleic acid from chicken anemia virus in the intact blood cell by nucleic acid hybridization. In a preferred embodiment, CAV nucleic acid is detected in a lymphocyte containing peripheral blood smear or cytospin buffy coat preparation by in situ hybridization.

DETAILED DESCRIPTION OF THE INVENTION

The present invention may be understood more readily by reference to the following detailed description of specific embodiments included herein. Although the present invention has been described with reference to specific details of certain embodiments thereof, it is not intended that such details should be regarded as limitations upon the scope of the invention. The entire text of the references mentioned herein are hereby incorporated in their entireties by reference.

As used in the claims, "a" may mean one or more than one, depending upon the context within which it is used. The term "in situ hybridization" as used herein includes any of the methods known in the art for detecting the presence of specific nucleic acid sequences in cells including, but not limited to techniques described in Mitchell et al.[25] and Martinez et al.[27]

The present invention provides a method for detecting the presence of a predetermined infectious agent in a subject comprising obtaining a preselected portion of a whole blood sample containing an intact blood cell from the subject and detecting the presence of a nucleic acid from the predetermined infectious agent in the intact blood cell by nucleic acid hybridization. The "predetermined infectious agent" can be any infectious agent which is or can be present within a blood cell including, but not limited to bacteria and viruses. Examples of such infectious agents include HIV virus, rotavirus, chicken anemia virus, equine infectious anemia virus, various bacterial pathogens such as *Escherichia coli* and Salmonella and blood borne pathogens such as Anaplasma sp., Babesia sp. and Rickettsia sp. Other examples of infectious agents which can be present within a blood cell are known in the art and can be found in Piper and Unger[7].

The phrase "preselected portion of a whole blood sample" is meant to include, but not be limited to any portion of a blood sample obtained from a human or animal subject which contains at least one detectable intact blood cell. The blood cell can be any blood cell including, but not limited to red blood cells and their precursors, white blood cells such as neutrophils and lymphocytes, thrombocytes and platelets, macrophages and the like. In one embodiment, the preselected portion of the blood sample is a peripheral blood smear. In yet another embodiment, the preselected portion is a cytospin buffy coat preparation or an intact lymphocyte.

Although the preferred embodiment utilizes nucleic acid probes in situ hybridization for the detection of nucleic acid from a predetermined infectious agent within a blood cell of a human or animal subject, the present invention specifically contemplates other forms of nucleic acid detection which can be adapted to be performed on the a blood cell. Moreover the present invention is not intended to be limited to nucleic acid detection in only intact blood cells. For example, the intact cells of a cytospin buffy coat preparation may be lysed before detection methods are utilized.

Other methods of nucleic acid detection known in the art such as polymerase chain reaction (PCR) with or without restriction fragment length polymorphism (RFLP) analysis, ligase chain reaction, and PCR reaction of specific alleles (PASA) can be utilized to enhance the subject assay and are described for example in Sambrook et al.[22].

The above method for detection of the predetermined infectious agent can specifically comprise contacting the preselected portion of the whole blood sample with at least one detectable nucleic acid probe that is selective for the agent under conditions favorable for promoting hybridization of the probe to the predetermined infectious agent in an intact blood cell and detecting the presence of the hybridization between the probe and the nucleic acid from the infectious agent, thereby detecting the presence of the predetermined infectious agent in the sample.

Conditions which are favorable for promoting hybridization of the particular probe to the nucleic acid of the preselected infectious agent can vary depending upon the infectious agent or portion of blood being utilized or the type of probe utilized. However, such conditions are generally known in the art and will be apparent to the skilled artisan.[20, 22,25,26,27] Thus, one can merely adapt the procedures set forth in the Examples to suit the preselected infectious agent.

In particular, the present invention provides a method for detecting the presence of chicken anemia virus in a chicken comprising utilizing a preselected portion of a whole blood sample containing a whole blood cell obtained from the chicken and detecting the presence of a nucleic acid from chicken anemia virus in the whole blood cell by nucleic acid hybridization. The preselected portion of the whole blood sample can be any portion which contains at least one detectable intact cell, including but not limited to peripheral blood smears and cytospin buffy coat preparations. In a preferred embodiment, the preselected portion is a lymphocyte.

In particular, the method can comprise detection of chicken anemia virus utilizing in situ hybridization. The method can specifically comprise the steps of contacting the preselected portion with at least one detectable nucleic acid probe selective for chicken anemia virus under conditions which are favorable for promoting hybridization of the probe to chicken anemia virus nucleic acid and detecting the presence of the hybridization between the probe and the chicken anemia virus nucleic acid, thereby detecting the presence of chicken anemia virus in the chicken.

Also provided by the invention are synthetic oligonucleotide probes which are selective for chicken anemia virus. Examples of such probes include, but are not limited to the nucleotide sequences set forth in the Sequence Listing as SEQ ID NO. 1 and SEQ ID NO. 2. It is specifically contemplated that the probes of SEQ ID NO. 1 and SEQ ID NO. 2 can be used alone or in combination with each other or another suitable probe in the above methods.

In general, primers and probes for PCR, LCR and in situ hybridization are usually about 20 bp in length and the preferable range is from 15–25 bp however longer probes can be utilized. Methods for synthesizing probes and primers from known conserved sequences of the predetermined infectious agent are known in the art.[22,26] Better amplification is obtained when both primers are the same length and with roughly the same nucleotide composition. Denaturation of strands usually takes place at 94 C and extension from the primers is usually at 72 C. The annealing temperature varies according to the sequence under investigation. Examples of reaction times are: 20 mins denaturing; 35 cycles of 2 min, 1 min, 1 min for annealing, extension and denaturation; and finally a 5 min extension step. Conditions favorable for hybridization of probes to a target nucleic acid are known in the art, e.g., Allen et al. Mitchell et al., Piper and Unger, and Maniatis et al.[20,22,25,26] and are set forth in the examples.

The probes provided herein may be suitably labeled using, for example, a radio label, enzyme label, fluorescent label, biotin-avidin label and the like for subsequent visualization. Specific examples are set forth in Mitchell et al.[25]

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

Example 1

In situ hybridization for detection of CAV in blood smears
Method
Preparation of Samples for Hybridization Blood smears from known CAV positive and known CAV negative chickens were obtained from SPAFAS, Inc. (Storrs, Conn.). Blood smears were fixed in 4% paraformaldehyde for 30 minutes, washed in TRIS-saline (0.1 M TRIS-Cl pH 7.5, 0.1 M NaCl), and dehydrated in graded 30, 60, 80, 95, 100% ethanol series. Dry slides were stored in sealed container at 4° C. prior to hybridization. The ability to interact with hybridization probe was not adversely affected by keeping slides stored under these conditions.

Hybridization probe

First Probe: A cocktail of two synthetic oligonucleotides, 5' TCG CAC TAT CGA ATT CCG AGT G 3' set forth in the Sequence listing as SEQ ID NO. 1 and 5' GGC TGA AGG ATC CCT CAT TC 3', set forth in the Sequence Listing as SEQ ID NO. 2 was used for in situ hybridization. The oligonucleotide sequences were derived from the CAV DNA sequence described by Noteborn et al.[21], and synthesized at the Molecular Genetics Facility at the University of Georgia. Oligonucleotides were digoxigenin and biotin labeled by 3' end-labeling reaction described by Maniatis et al.[22]. To the hybridization cocktail, containing 45% formamide, purchased from Amresco (Solon, Ohio), was added 0.5 $\mu$g/ml labeled probe.

Second Probe: A DNA fragment of CAV was amplified by PCR using oligonucleotide primers 5' TCG CAC TAT CGA ATT CCG AGT G 3' SEQ ID NO: 1 and 5' GGC TGA AGG ATC CCT CAT TC 3' SEQ ID NO:2. These oligonucleotide sequences were derived from the CAV DNA sequence described by Noteborn et al.[27], and they were synthesized at the Molecular Genetics Facility at The University of Georgia. The template for amplification of probe by PCR was DNA extracted from MDCC-MSB 1 cells using proteinase K (1 mg/ml proteinase K, 1 mM EDTA, 10 mM TRIS, pH 8, 1% SDS) for 2 hours at 37° C., followed by extraction with phenol:chloroform: isoamyl alcohol (25:24:1), chloroform:isoamyl alcohol (24:1), and precipitation with ethanol at −20° C. Polymerase chain reaction was carried out in 100 $\mu$l volumes, which included 0.5 $\mu$g of each primer, 10 $\mu$l of extracted DNA, deoxyribonucleotides in final concentration of 100 $\mu$M each (Pharmacia, Piscataway, N.J.), Taq polymerase (Promega, Madison, Wis.), and 2 mM $MgCl_2$. A Perkin-Elmer thermal cycler was programmed to carry out a 2 minute denaturation step at 94° C., followed by 25 cycles composed of 2 minutes at 94° C., 1 minute at 47° C., and 3 minutes at 72° C. A final extension period of 7 minutes at 72° C. was followed by storage at 4° C. Amplified DNA was extracted from the PCR reaction mixture following the same procedure described for extraction of DNA from CAV infected cells omitting incubation with proteinase K. The amplified fragments of CAV DNA were labeled with digoxigenin-11dUTP (Boehringer Mannheim, Indianapolis, Ind.) or biotin-11-dUTP (Boehringer Mannheim) by the nick translation method[28]. Unincorporated nucleotides were removed by gel filtration using Quick Spin Columns (Boehringer Mannheim). The integrity of PCR product and success of the labeling procedure were confirmed by dot-blot hybridization[28] of known CAV DNA template using uninfected cell DNA as negative control.

Pretreatment for in situ hybridization

Blood smears were hydrated in graded 100, 95, 80, 60, 30% ethanol series, soaked briefly in TRIS-saline, and placed for 10 minutes in 0.02 N HCl. After two washes in TRIS-saline, 3 minutes each, slides were incubated 1.5 minutes in PBS containing 0.01% Triton X-100. Following two washes in TRIS-saline, lasting 3 minutes each, the slides were incubated for 5 to 10 minutes (digestion was controlled visually under a microscope) in pronase (0.5 mg/ml) dissolved in 0.05 M Tris-HCl buffer, pH 7.6, containing 5 mM EDTA. After washing twice for 3 minutes in TRIS-saline containing 2 mg/ml glycine, smears were post-fixed in 4% solution of paraformaldehyde in TRIS-saline, washed twice for 3 minutes in TRIS-saline with 2 mg/ml glycine, and dehydrated through a graded ethanol series (30, 60, 80, 95, and 100%—twice each for 5 minutes) and finally air dried.

Hybridization

The hybridization cocktail previously prepared was spotted over the blood smears and covered with autoclavable coverslips. Smears and the probe were denatured by heating the slides at 110° C. for 10 minutes. The slides were then incubated for two hours at 37° C. hen hybridization was complete, slides were dipped in 2× SSC and first washed twice in 2× SSC 0.1% SDS, twice in 0.2× SSC 0.1% SDS, twice in 0.1× SSC 0.1% SDS, for 3 minutes each step. Next they were washed once for 1 minute in 2× SSC 0.1% SDS, and then incubated for 5 minutes in 3% BSA in TRIS-Cl, pH 7.5, 0.1 M NaCl, 5 mM $MgCl_2$, 0.25% Brij (TRIS-saline Brij, pH 7.5). Following the wash steps the slides were air dried.

Colorimetric detection

Blocked blood smears, hybridized with biotin labeled probe, were incubated for 5 minutes at room temperature in an avidin-alkaline phosphatase complex. The avidin-alkaline phosphatase complex had been freshly prepared by combining 40 $\mu$m Avidin DN (Vector Laboratories, Burlingame, Calif.), 5 $\mu$l of biotinylated alkaline phosphatase (Boehringer-Mannheim, Indianapolis, Ind.) and 11 ml 1% BSA in TRIS-saline Brij, pH 7.5. Blood smears, hybridized with digoxigenin-labeled probe, were incubated for 20 minutes at 37° C. with anti-digoxigenin-alkaline phosphatase Fab fragment (Boehringer Mannheim) diluted 1:600 in TRIS-saline Brij, pH 7.5, containing 1% BSA.

Smears, hybridized with biotin- and digoxigenin-labeled probes, were after this step washed three times for 3 minutes in TRIS-saline Brij, pH 7.5, and once in TRIS-saline Brij pH, 9.5 (0.1 M TRIS-Cl, pH 9.5, 0.1 M NaCl, 50 mM $MgCl_2$). Color was developed by incubating slides for 2 hours at 37° C. in McGadey reagent[23]. The McGadey reagent had been freshly prepared by adding 67 $\mu$l of 50 mg/ml 50% N,N-dimethyl formamide stock solution of nitro blue tetrazolium and 33 $\mu$l of 50 mg/ml 50% N,N-dimethyl formamide stock solution of 5-bromo-4-chloro-3-indoyl phosphate p-toluidine salt to 10 ml TRIS-saline, pH 9.5.

The slides were washed three times for 1 minute in TRIS-saline, pH 7.5, counterstained with nuclear fast red, air dried, and mounted in 70% Permount (Fisher Scientific, Norcross, Ga.) diluted with xylene.

Results

Following processing by in situ hybridization, blood smears obtained from chickens infected with CAV contained positive lymphocytes with clearly noticeable signal produced by alkaline phosphatase with McGadey reagent in the form of dark-blue formazan crystals. Due to relatively weak signal, as a result of using cocktail of synthetic oligonucleotides as a probe, signal developed slowly. The optimal ratio between signal and background was obtained after two hours of incubation at 37° C. Hybridization was considered positive when one or more cells had unambiguous nuclear or cytoplasmic staining. Nonspecific staining, when it occurred, consisted of dark dots in a random pattern dispersed in spaces between blood cells.

Blood smears from uninfected chickens occasionally showed some nonspecific staining, but on higher-power examination, this staining was easily distinguished by its extracellular location. To exclude any staining possibly due to endogenous alkaline phosphatase activity, the avidin-enzyme complex was omitted from colorimetric detection procedure. Blood smears stained following this procedure showed no color development.

Thus, In situ hybridization for detection of CAV in blood smears, in addition to providing rapid results, requires very simple sample collection and is convenient for quick screening of large numbers of birds.

Example 2
In situ hybridization for detection of retrovirus HIV
Method Selected oligonucleotides specific for the retrovirus HIV were synthesized with biotin bound at the 5' end. The sequences were: oligonucleotide 1, 5' ATC CTG GGA TTA AAT AAA ATA GTA AGA ATG TAT AGC CCT AC 3' SEQ ID NO:3; oligonucleotide 2, 5' CAA TGA GAC ACC AGG GAT TAG ATA TCA GTA CAA 3' SEQ ID NO:4; oligonucleotide 3, 5' ATG GGT GCG AGA GCG TCA GTA TTA AGC G 3' SEQ ID NO:5; oligonucleotide 4, 5' AAT CCT GGC CTG TTA GAA ACA TCA GAA G 3' SEQ ID NO:6: oligonucleotide 5, 5' CGC TTA ATA CTG ACG CTC TCG CAC CCA T 3' SEQ ID NO:7; oligonucleotide 6, 5' GGG AGC TAG AAC GAT TCG C 3' SEQ ID NO:8. A cocktail of all six oligonucleotides was made in water and contained 0.167 μg/μl of each oligonucleotide.

Results

Cytospin preparations of peripheral blood monocytes from chimpanzees that were infected and those that were not infected with HIV-1 were prepared on glass microscope slides. Cytospin preparations also were prepared with cultured cells infected with one copy of HIV-I or HTLV-1. The cytospin preparations were fixed in paraformaldehyde, treated with pronase and postfixed with paraformaldehyde as described in example for CAV. Hybridization and color detection were as described in example for CAV. Positive staining was observed by light microscopy on cells from infected chimpanzees and cells infected in culture with HIV-I, but not from uninfected chimpanzees or cells infected in culture with HTLV-I.

Example 3
Competitive spectrophotometric detection of nucleic acids in microtiter plates
Method
Immobilization of nucleic acids on microtiter plates An unlabeled probe for the nucleic acid of interest must first be denatured prior to immobilization. When the probe is DNA, it is may be denatured by two different methods. In the first method denaturing is done by the boiling of DNA suspension (1 μg/50 μl) in TE buffer (10 mM Tris5 1 mM EDTA) for 10 minutes in a water bath. In a second method the DNA suspension is first combined with 40 μl (20 μg) of DNA probe, 75 μl 2M NaOH and 385 μl dH$_2$O, next it is heated at 65° C. for one hour, cooled to room temperature and finally 500 μl 2M ammonium acetate, pH 7.0 is added.

Denaturing of RNA probe is most commonly achieved by combining 10 μl suspension of RNA (2.4 μg dissolved in dH$_2$O) with 20 μl 100% formamide, 7 μl 37% formaldehyde, and 2 μl 2× SSC. The mixture is then incubated at 68° C. for 15 minutes, followed by cooling on ice. Two volumes (78 μl) of 20× SSG are added to complete the denaturing process.

To immobilize denatured nucleic acids in the wells, 1 μg of denatured nucleic acid (50 μl) is pipetted into the well and 50 μl of immobilization buffer (1.5M NaCl, 0.3M TrisHCl, pH 8.0; 0.3M MgCl$_2$) is added. Plates are incubated overnight at 37° C. The denatured nucleic acid mixture is then removed from the wells, and the wells are allowed to dry for 30 minutes at 37° C. The wells are irradiated at 254 nm and washed three times with washing buffer (1M NaCl;, 0.1M Tri-HCl, pH 9.3; 2 mM MgCl$_2$; 0.1% Tween 20). Other methods of immobilization are well known to those of ordinary skill in the art.

Wells containing immobilized, denatured nucleic acids can be used immediately or stored at 4° C. in a sealed bag.

Preparation of samples for hybridization

Anticoagulated blood samples (500 μL) were mixed with 1 ml of 37.5 mM NaCl and centrifuged at 800 g for 5 minutes at 4° C. to collect cells at the bottom of the tube. The supernatant was discarded and the pellet was washed several times with the salt solution to eliminate the majority of hemoglobin. Cells suspended in 37.5 mM NaCl were then frozen and thawed. 100 ul of 0.5 M NaOH and 5M NaCl were added to 400 μl of the sample to release and denature the DNA. The samples were mixed well and incubated for one hour at 37° C.

Prehybridization

To each well of microtiter plate was added 100 μl of prehybridization solution containing 6× SSC (0.9 M NaCl, 0.09 M Na citrate), 5× Denhardt's solution, 0.01 M EDTA and 0.5% SDS. The plates were then incubated for one hour at 56° C.

Hybridization

A mixture consisting of 1.73 ml deionized 100% formamide, 0.96 ml 20× SSC, 38 μl 100× Denhardt's solution, 154 μl 0.5 M Na phosphate, pH 6.5, 77 μl of 10 mg/ml freshly denatured sheared herring sperm DNA, 385 μl 50% dextran sulfate, and 400 μl of sample, (as described above) was prepared. 100 μl of the mixture was next pipetted into each well and the plates were then incubated for two hours at 56° C. After hybridization, the hybridization cocktail was discarded and the plates were washed three times for 3–5 minutes at room temperature in 2× SSC, 0.25% Brij, and 0.1% SDS followed by two washes in 0.2× SSC, 0.25% Brij, 0.1% SDS at 56° C. for 10–20 minutes. The plates were then rinsed in prehybridization solution.

100 μl of hybridization cocktail containing 45% formamide, 5× SSC, 1× Denhardt's solution, 20 mM sodium phosphate, pH 6.S, 0.2 mg/ml freshly denatured sheared herring sperm DNA, 5% dextran sulfate, and 0.5 μg/ml biotinylated probe (for example, the present invention is not limited to a specific probe and includes any type of label) was then added to the plates. After incubation at 56° C. for two hours, the hybridization cocktail was removed from the plates and the plates were rinsed briefly with 2× SSC. The plates were washed two times for 5 minutes each in 2× SSC, 0.25% Brij, and 0.1% SDS and two times for 10–20 minutes each at 56° C. in 0.2× SSC, 0.25% Brij, and 0.1% SDS.

Next 2% BSA in TS Brij, pH 7.5 was added to the plates. After incubation at room temperature for 10 minutes the BSA solution was discarded and 100 μl per well of avidin-biotin-alkaline phosphatase complex (40 μL of 1.0 mg/ml avidin and 5 μl of 2000 U/ml of biotin-alkaline phosphatase in 2% BSA in TS Brij, pH 7.5) was added. The plates were then incubated for 10 minutes at room temperature.

Finally the plates were washed three times in TS Brij pH 7.5 (0.1 M Tris-Cl pH 7.5, 0.1 M NaCl, 5 mM MgCl$_2$, 0.01% Brij), and once in TS Brij, pH 9.5 (0.1 M Tris-HCl, pH 9.5, 0.1 M NaCl, 50 mM MgCl$_2$).

Colorimetric Detection

Preparation of the substrate solution consisted of mixing p-nitrophenyl phosphate (0.75 mg/ml) in diethanolamine-Cl buffer, pH 9.8 (0.1 g MgCl$_2$×6H$_2$, O and 96 ml diethanolamine in 11 dH$_2$O). 100 μl of substrate solution was added per well and incubated at room temperature for one hour. The absorbance was measured at 410 nm. Amounts of immobilized, unlabeled probe and labeled soluble probe were adjusted to obtain optimal signal (absorbance, fluorescence, chemiluminescence and the like, depending on labeling system used) which for absorbance systems is between 0.2–2.0 absorbance units. Positive control (nucleic acid extract of cells infected with virus) and test sample, if containing viral nucleic acid, cause significant decrease in absorbance by competition with soluble, labeled probe, whereas negative control (nucleic acid extract from uninfected cells) does not.

REFERENCES

The entire text of the following references is including any citations to other works contained therein are hereby incorporated by reference:

1. Yuasa, N., Taniguchi, T. & Yoshida, I. (1979). Isolation and some properties of an agent inducing anemia in chicks. Avian Diseases, 23, 366–385.
2. Gelderblom H., Kling, S., Lurz, R., Tischer, I. & Bulow, V. von (1989). Morphological characterization of chicken anemia agent (CAA). Archives of Virology, 109, 115–120.
3. Todd, D., Creelan, J. L., Mackie, D. P., Rixon, F. & McNulty, M. S. (1990). Purification and biochemical characterization of chicken anemia agent. Journal of General Virology, 71, 819–823.
4. Taniguchi, T., Yuasa, N., Maeda, M. & Horiuchi, T. (1982). Haematopathological changes in dead and moribund chicks induced by chicken anemia agent. National Institute of Animal Health Quarterly, Japan, 22, 61–69.
5. Taniguchi, T., Yuasa, N., Maeda, M. & Horiuchi, T. (1983). Chronological observations on haematopathological lesions in chicks inoculated with chicken anemia agent. National Institute of Animal Health Quarterly, Japan, 23, 1–12.
6. Bulow, V. von, Fuchs, B. & Bertram, M. (1985). Untersuchungen uber den Erreger der infektiosen Anamie bei Huhnerkuken (CAA) in vitro: Vermehrung, Titration, Serumneutralisationstest und indirekter Immunofluoreszenztest. Journal of Veterinary Medicine, B, 32, 679–693.
7. Yuasa, N., Imai, K., Watanabe, K., Saito, F., Abe, M. & Komi, K. (1987). Aetiological examination of an outbreak of haemorrhagic syndrome in a broiler flock in Japan. Avian Pathology, 16, 521–526.
8. Jeurissen, S. H. M., Pol, J. M. A. & De Boer, G. F. (1989). Transient depletion of cortical thymocytes induced by chicken anemia agent. Thymus, 14, 115–123.
9. Otaki, Y., Nunoya, T., Tajima, M., Tamada, H. & Nomura, Y. (1987). Isolation of chicken anemia agent and Marek's disease virus from chickens vaccinated with turkey herpesvirus and lesions induced in chickens by inoculating both agents. Avian Pathology, 16, 291–306.
10. Cloud, S. S., Lillehoj, H. S., Rosenberger, J. K. (1992a). Immune dysfunction following infection with chicken anemia agent and infectious bursal disease virus I. Kinetic alterations of avian lymphocyte subpopulations. Veterinary Immunology and Immunopathology, 34, 3–4.
11. Cloud, S. S., Rosenberger, J. K., Lillehoj, H. S. (1992b). Immune dysfunction following infection with chicken anemia agent and infectious bursal disease virus II. Alterations of in vitro lymphoproliferation and ND in vivo immune responses. Veterinary Immunology and Immunopathology, 34, 353–366.
12. Bounous, D. I., Goodwin, M. A., Brooks, R. L. Jr et al.(1995). Immunosuppression and intracellular calcium signaling in splenocytes from chicks infected with chicken anemia virus, CL-1 isolate. Avian Diseases, 39, 135–140.
13. Yuasa, N., Taniguchi, T. & Yoshida, I. (1980). Effect of infectious bursal disease virus infection on incidence of anaemia by chicken anemia agent. Avian Diseases, 24, 202–209.
14. Bulow, V. von, Rudolph, R. & Fuchs, B. (1986). Folgen der Doppelinfektion von Kuken mit Adenovirus oder Reovirus und dem Err ger der aviaren infektiosen Anamie (CAA). Journal of Veterinary Medicine, B, 33, 717–726.
15. Engstrom, B. E. (1988). Blue wing disease of chickens: isolation of avian reovirus and chicken anemia agent. Avian Pathology, 17, 23–32.
16. Rosenberger, J. K. & Cloud, S. S. (1989a) The effects of age, route of exposure and coinfection with infectious bursal disease virus on the pathogenicity and transmissibility of chicken anemia agent (CAA). Avian Diseases, 33, 753–759.
17. Rosenberger J. K. & Cloud, S. S. (1989b). The isolation and characterization of chicken anemia agent (CAA) from broilers in the Unites States. Avian Diseases, 33, 707–713.
18. McNulty, M. S. & Allan, G. M. (1984). Applications of immunofluorescence in veterinary viral diagnosis. In Recent advances in virus diagnosis. (McNulty, M. S. & McFerran, J. B., eds.) Pp. 15–26. The Hague: Martinus Nijhoff, Netherlands.
19. Noteborn, M. H. M., Verschueren, C. A. J., Van Roozelaar, D. J., Veldkamp, S., Van der Eb, A. J. & De Boer, G. F. (1992). Detection of chick en anaemia virus by DNA hybridization and polymerase chain reaction. Avian Pathology, 21, 107–118.
20. Allan, G. M., Smyth, J. A., Todd, D. & McNulty, M. S. (1993). In situ hybridization for the detection of chicken anemia virus in formalin-fixed, paraffin-embedded sections. Avian Diseases, 37, 177–182.
21. Noteborn, M .H. M., De Boer, G. F., Van Roozelaar, D. J. et al. (1991). Characterization of cloned chicken anemia virus DNA that contains all elements for the infectious replication cycle. Journal of Virology, 65, 3131–3139.
22. Sambrook et al. (latest issue) Molecular cloning: a laboratory manual. Cold Spring Harbor Laboratory, Cold Spring Harbor, N.Y.
23. McGadey, J.(1970). A tetrazolium method for non-specific alkaline phosphatase. Histochimie, 23, 180–184.
24. Yuasa, N., Taniguchi, T., Goda, M., Shibatanni, M., Imada, T. & Hihara, H. (1983). Isolation of chicken anemia agent with MDCC-MSB1 cells from chickens in the field. National Institute of Animal Health Quarterly, Japan, 23, 78–81.
25. Mitchell, B. S. Dhami, D. and Schumacher, U.(1992). In situ hybridization: a review of methodologies and applications in the biomedical sciences. Medical Laboratory Sciences 49: 107–118.
26. Piper, Margret A. and Unger, Elizabeth R. (1989). Nucleic Acid Probes: A Primer for Pathologists. ASCP Press, Chicago.
27. Martinez, A., Miller, M., Quinn, K., Unsworth, E., Ebino, E., and Cuttitta, F. (1995). Non-radioactive Localization of Nucleic Acids by Direct In situ PCR and In situ RT-PCR in Paraffin-embedded Sections. Journal of Histiochemistry and Cytochemistry, Vol. 43, No. 0, pp 0–00.

What is claimed is:

1. A method for detecting an infectious agent in a sample via detection of its nucleic acid comprising:

(a) immobilizing unlabeled and denatured double stranded nucleic acid probe onto a solid phase support;

(b) treating the sample, which is suspected of containing an infectious agent to denature any double stranded nucleic acid contained therein;

(c) adding the treated sample containing the nucleic acid to the immobilized probe;

(d) incubating the treated sample and immobilized probe so that any nucleic acid of the infectious agent therein hybridizes to complementary sequences of the immobilized probe;

(e) adding labeled nucleic acid probe competes with any nucleic acid of the infectious agent for hybridizing to the immobilized probe;

(f) washing any unhybridized labeled or unlabeled probe away the solid phase support;

(g) detecting any remaining immobilized label as an indication of the presence of the infectious agent in the sample.

2. The method of claim 1, wherein the infectious agent is selected from the group consisting of viruses and bacteria.

3. The method of claim 2, wherein the viruses comprise human immunodeficiency virus, rotavirus, chicken anemia virus or equine infectious anemia virus.

4. The method of claim 2, wherein the virus is chicken anemia virus.

5. The method of claim 2, wherein the bacteria comprises *Escherichia coli*, Salmonella sp., Anaplasma sp., Babesia sp. and Rickettsia sp.

6. The method of claim 1, wherein the label comprises a radioactive label, an enzyme label, a fluorescent label, a biotin label, an avidin label or a digoxigenin label.

* * * * *

SEQUENCE LISTING

<160> NUMBER OF SEQ ID NOS: 8

<210> SEQ ID NO 1
<211> LENGTH: 22
<212> TYPE: DNA
<213> ORGANISM: Chicken

<400> SEQUENCE: 1
tcgcactatc gaattccgag tg                                    22

<210> SEQ ID NO 2
<211> LENGTH: 20
<212> TYPE: DNA
<213> ORGANISM: Chicken

<400> SEQUENCE: 2
ggctgaagga tccctcattc                                       20

<210> SEQ ID NO 3
<211> LENGTH: 41
<212> TYPE: DNA
<213> ORGANISM: Human immunodeficiency virus

<400> SEQUENCE: 3
atcctgggat taaataaaat agtaagaatg tatagcccta c               41

<210> SEQ ID NO 4
<211> LENGTH: 33
<212> TYPE: DNA
<213> ORGANISM: Human immunodeficiency virus

<400> SEQUENCE: 4
caatgagaca ccagggatta gatatcagta caa                        33

<210> SEQ ID NO 5
<211> LENGTH: 28
<212> TYPE: DNA
<213> ORGANISM: Human immunodeficiency virus

<400> SEQUENCE: 5
atgggtgcga gagcgtcagt attaagcg                              28

<210> SEQ ID NO 6
<211> LENGTH: 28
<212> TYPE: DNA
<213> ORGANISM: Human immunodeficiency virus

<400> SEQUENCE: 6
aatcctggcc tgttagaaac atcagaag                              28

<210> SEQ ID NO 7
<211> LENGTH: 28
<212> TYPE: DNA
<213> ORGANISM: Human immunodeficiency virus

<400> SEQUENCE: 7
cgcttaatac tgacgctctc gcacccat                              28

<210> SEQ ID NO 8
<211> LENGTH: 19
<212> TYPE: DNA
<213> ORGANISM: Human immunodeficiency virus -continued

```
<400> SEQUENCE: 8
gggagctaga acgattcgc                                                    19
```